United States Patent [19]

Dawson et al.

[11] 4,039,571
[45] Aug. 2, 1977

[54] ORGANIC DERIVATIVES

[75] Inventors: William Dawson, Camberley; Michael John Foulis, Bracknell; Norman James Albert Gutteridge, Owlsmoor, near Camberley; Colin William Smith, Bracknell, all of England

[73] Assignee: Lilly Industries, Ltd., London, England

[21] Appl. No.: 637,782

[22] Filed: Dec. 4, 1975

[30] Foreign Application Priority Data

Dec. 9, 1974 United Kingdom ............... 53220/74

[51] Int. Cl.$^2$ ........................................... C07C 177/00
[52] U.S. Cl. .................. 260/468 D; 195/30; 260/347.3; 260/347.4; 260/448.8 R; 260/468 K; 260/473 A; 260/476 R; 260/488 R; 260/514 D; 260/514 K; 260/520 B; 542/429; 542/430; 181/305; 181/317
[58] Field of Search .......... 260/468 K, 468 D, 514 K, 260/514 D, 514 C, 514 A

[56] References Cited

PUBLICATIONS

Boot et al., Prostaglandins, 8 439 (1974).

Primary Examiner—Robert Gerstl
Attorney, Agent, or Firm—Kathleen R. S. Page; Everet F. Smith

[57] ABSTRACT

Propanoic acid derivatives of formula:

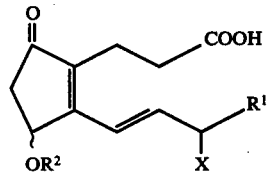

where X represents a ketonic or hydroxylic function, $R^1$ is a $C_{1-8}$ alkyl group optionally substituted by hydroxy or —COOH and $R^2$ is hydrogen or a protecting group, having spasmolytic activity.

7 Claims, No Drawings

ORGANIC DERIVATIVES

This invention relates to a class of novel propanoic acid derivatives substituted in the three-position by a cyclopentenyl group, to a class of novel propanoic acid intermediates, to a method of preparing such intermediates and to a method of preparing said novel derivatives from said novel intermediates. The novel compounds of the invention possess useful pharmacological activity and accordingly the present invention also provides pharmaceutical compositions comprising one or more of said novel compounds.

In the specification of our co-pending Application Ser. No. 459,829, filed Oct. 4, 1974, there is described inter alia the preparation of compounds having the structure:

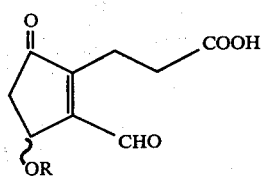
(I)

and salts and esters thereof, where R is hydrogen, acyl or benzoyl. As stated in said specification, the foregoing compounds may exist in racemic or optically active form and are useful as antithrombotic agents.

It has now been discovered that the above compounds of formula (I) can be converted by means of the well-known Wittig reaction into a class of intermediate propanoic acid derivatives which can be reduced to provide a novel class of propanoic acid derivatives possessing useful and valuable pharmacological activity.

According to a first aspect of the present invention there is provided a compound of formula (II):

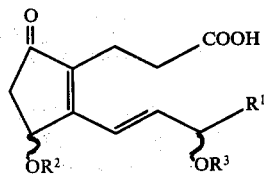
(II)

wherein $R^2$ and $R^3$ are individually hydrogen or a protecting group for example an acyl, tetrahydropyranyl, trialkylsilyl, or aroyl, such as benzoyl, group; $R^1$ is a straight or branched alkyl group having from 1 to 10 atoms and being optionally substituted by a hydroxyl or COOH group or is an optionally substituted phenyl group; or a salt or ester thereof.

The compound of formula (II) may exist in racemic or optically active form. It is preferred that the substituents about the exocyclic double bond, be in a trans-configuration. Compounds of formula (II), particularly the monocarboxylic acid, in which $R^1$ represents an n-pentyl group are particularly preferred. Also preferred are compounds of formula (II) in which $R^2$ and/or $R^3$ represent hydrogen.

The compounds of formula (II) have been found to possess useful spasmolytic activity coupled with low toxicity.

According to a second aspect of the present invention there is provided a method of preparing a compound of formula (II) or a salt or ester thereof, which comprises reducing a compound of formula (III):

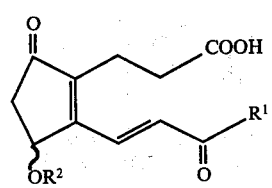
(III)

wherein $R^1$ and $R^2$ are as defined above, or a salt or ester thereof, followed by one or more of the following optional steps:

a. where $R^2$ in the compound of formula (II) is a hydrogen atom, protecting the endocyclic hydroxyl group;
b. salifying or esterifying a resultant free acid of formula (II);
c. desalifying or deesterifying a resulting salt or ester of formula (II);
d. where $R^2$ is a protecting group in the resultant compound of formula (II) removing said group to form a compound of formula (II) in which $R^2$ represents a hydrogen atom;
e. when it is desired to form a compound of formula (II) in which $R^3$ is a protecting group, reacting the hydroxyl product of the reduction with a suitable protecting agent; and
f. resolving into its enantiomorphs a resultant racemic mixture of compounds of formula (II).

The Applicants have found that the exocyclic carbonyl group in the above system is significantly more reactive than the endocyclic carbonyl group and thus that by the choice of suitable quantities of reagents and reaction conditions, reduction of the endocyclic carbonyl group can be substantially avoided.

The reduction of (III) can be accomplished by chemical or microbial means. When the reduction is carried out by chemical means any reducing agent which reduces carbonyl groups rather than or before carbon-carbon olefinic double bonds can be utilised. Such reducing agents are well-knonw to those skilled in the art but it may be mentioned that borohydrides such as sodium or potassium borohydride have been found to be particularly useful.

The exocyclic carbonyl group can also be reduced by means of microbial reduction using, for example *Pseudomonas* species. However, it should be noted that such reduction is stereo-specific. In other words, the reduction by microbial means is only effective for certain of the stereoisomers of compounds of formula (III). For example, reduction of a racemic mixture of the compound of formula:

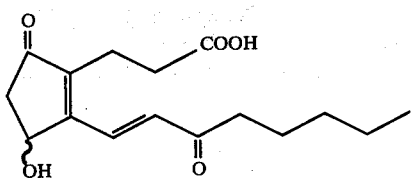

with *Pseudomonas* species (N.R.R.L. B-3875) results in the formation of the compound of formula:

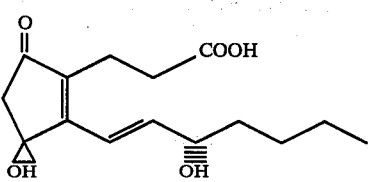

A suitable medium for the microbial reduction is a medium containing a sugar such as glucose although any of the well-established growth media for this kind of bacteria can be used.

The compounds of formula (III), and salts and esters thereof, are themselves novel compounds, and are thus provided in a further aspect of the invention. As well as being useful intermediates, these compounds are of pharmacological interest in their own right since they also possess spasmolytic activity coupled with low toxicity.

Compounds of formula (II) and (III) can be labelled, i.e. one or more of the carbon, hydrogen or oxygen atoms may be in the form of one of their less common, even radioactive, isotopes. For example, one or more of the hydrogen atoms can be deuterium or tritium, or one or more of the carbon atoms may be $C^{13}$ or $C^{14}$ atoms. Such labelled compounds have value as diagnostic agents, for instance, in GCMS isotope dilution assays.

The labelled atom can be introduced into the compound of formula (II) or (III) at any stage in the synthesis. The methods by which the labelled atom can be introduced are well-known in the art, see for example, "Organic Syntheses with Isotopes" by A. Murray (III) and D. L. Williams, Parts I and II, published in 1958 by Interscience, New York and London. According to yet a further aspect of the present invention there is provided a method of preparing a compound of formula (III) which comprises reacting a compound of formula (IV):

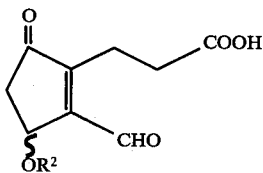

(IV)

wherein $R^2$ is as defined above, or salt or ester thereof, with a Wittig reagent of formula:

ZCHCOR¹          (V)

wherein Z indicates the phosphorus moiety of the Wittig reagent and wherein $R^1$ is as defined previously, or salt or ester thereof.

The Wittig reaction between an aldehyde and a Wittig reagent is a very well-known and understood chemical reaction (see, for example, page 1226 of the Merck Index, eighth edition). Those skilled in the art will readily appreciate that phosphoranes of formula:

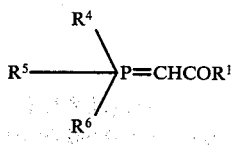

where $R^4$, $R^5$, and $R^6$ represent optionally substituted phenyl groups or alkyl groups such as n-butyl (see *J. Org. Chem.*, 1973, 38, 4415) can be used in the reaction.

As is well known, these phosphoranes can be generated in situ from the corresponding phosphonium salt in the presence of an aqueous base. The phosphoranes can be prepared from a triphenyl methyl phosphonium bromide of formula:

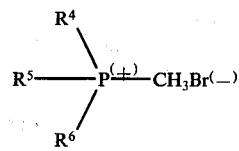

and $R^1$ COCl or an equivalent anhydride, in the presence of n-butyl lithium using an inert solvent system. Other halides can be used in place of the bromide. As is indicated above, the preparation of phosphoranes of the above type is well-documented, see for example *Journal of Organic Chemistry*, 1957, 22, 41; and *Journal of Organic Chemistry*, 1972, 37, 1818.

Any suitable inert solvent system can be used for the reaction. One such solvent system is dry tetrahydrofuran. This may be used in conjunction with chloroform. Alternatively, the solvent can be a mixture of dioxan and benzene.

Z can also represent the reactive entity derived from the kind of Wittig reagent known by the term Corey's reagent (see Corey, et al., *Journal of the American Chemical Society*, 1968, 90, 3247).

This reactive entity can be produced in situ from a Corey's reagent of formula:

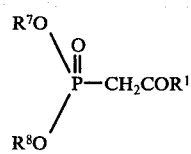

where $R^1$ is as defined above, and $R^7$ and $R^8$ are $C_{1-4}$ alkyl groups, preferably methyl, by treatment with sodium hydride in an inert solvent.

The Wittig reaction described above, results in the production of a compound in which the substituents about the exocyclic carbon-carbon olefinic double bond are in a transconfiguration. These are the preferred compounds of the invention.

To accomplish the Wittig reaction it is preferred that the reaction be carried out under an inert gas atmosphere such as nitrogen. At reflux temperatures, the reaction is normally complete after 3 or 4 hours: however, if desired, the reaction mixture can be refluxed overnight without ill-effect.

The salts of the acids of formula (II) or (III) are preferably alkali metal salts such as the sodium or potassium salts, the preparation of which can be accomplished by reaction of the acid with an appropriate base such as an alkali metal hydroxide, carbonate or hydrogen carbonate. In addition, the salt may be an amine salt such as a tertiary amine salt, for example, that formed from triethylamine.

Examples of suitable esters of the acids of formula (II) or (III) include alkyl, silyl, cycloalkyl, cycloalkyl-alkyl, aralkyl, heteroaryl-alkyl, alkylaminoalkyl and alkoxyalkyl esters. Preferred esters are the $C_{1-4}$ alkyl esters optionally substituted by one or more halogen atoms such as the methyl, ethyl, n-propyl, isobutyl, t-butyl, chloromethyl, trifluoromethyl, 2-chloroethyl and 2,2,2-trichloroethyl esters. The preparation can be carried out in conventional manner, for example, by reacting the free acid of formula (II) or (III) with an appropriate alcohol in the presence of an acid catalyst. Thus, the preferred esters of the invention may be prepared by reaction with, for example, methanol, ethanol, isopropanol, t-butanol, chloromethanol or 2,2,2-trichloroethanol in the presence of p-toluene sulphonic acid. The $C_{1-4}$ alkyl esters of the invention may also be prepared by reaction of the free acid with a diazoalkane such as a diazomethane or diazoethane.

When $R^2$ in formula (II) or (III) above is an acyl or aroyl group such as benzoyl, the preferred examples of such groups are $C_{2-4}$ acyl, $C_{2-4}$-haloacyl, benzoyl, nitrobenzoyl, halobenzoyl, $C_{1-4}$ alkyl-benzoyl, and $C_{2-4}$ alkoxybenzoyl, and especially acetyl, propionyl, chloroacetyl, 3,3,3-trichloropropionyl, benzoyl, p-nitrobenzoyl, p-methylbenzoyl, p-chlorobenzoyl, and p-methoxybenzoyl. If $R^2$ is hydrogen in the starting material of formula (III) and hence the end product of formula (II), the latter may readily be converted to a compound of formula (II) in which $R^2$ is an acyl or aroyl group by reaction with an appropriate acylating or aroylating agent, for example, an acyl or benzoyl halide, or an acid anhydride such as acetic anhydride, propionic anhydride, 3,3,3-trichloropropionic anhydride, acetyl chloride, benzoyl chloride, p-chlorobenzoyl chloride or p-nitrobenzoyl chloride. The above acylation or aroylation is preferably carried out on the ester.

If it is desired to prepare a compound of formula (II) or (III) in which $R^2$ is a tetrahydropyranyl group, such compounds can be prepared by reacting a compound of formula (IV), where $R^2$ is hydrogen, with 2,3-dihydropyran in an inert solvent such as tetrahydrofuran in the presence of a mineral acid such as hydrochloric acid as catalyst. This compound of formula (IV) can then be reacted with the phosphorane of formula (V) followed, if desired, by reduction to yield corresponding tetrahydropyranyl ethers of formula (II) or (III).

Alternatively, a compound of formula (II) or (III) in which $R^2$ represents a hydrogen atom can be reacted with 2,3-dihydropyran using the above reaction conditions to give a tetrahydropyranyl ether of formula (II) or (III). The tetrahydropyranyl group is easily removable, for instance, by acid hydrolysis using, for example, aqueous acetic acid.

$R^2$ in the compounds of formula (II) and (III) may also be a trialkylsilyl, preferably the trimethylsilyl, group. Such compounds can be prepared by reacting a compound of formula (II) or (III), where $R^2$ is hydrogen, with, for example, chlorotrimethyl silane in the presence of 1,1,1-3,3,3-hexamethyldisilazane using an inert anhydrous solvent such as tetrahydrofuran. Such methods are well-known in the art, see for example, E. J. Corey, et al., *Journal of the American Chemical Society*, 94, 17, 6190-1. The trialkyl silyl group can be removed by hydrolysis.

Compounds of formula (II) in which $R^3$ represents a protecting group can be prepared in a similar manner to that described above for $R^2$ protecting groups, i.e. by reaction of the exocyclic hydroxyl group with an appropriate protecting agent. However, it should be noted that, of course, only the compound of formula (II) contains the protectible exocyclic hydroxyl group and thus the protecting group $R^3$ can only be introduced after the reduction of the compound of formula (III).

When the compound of formula (II) or (III) is in the ester form, the ester group can be converted to the free carboxylic acid group by hydrolytic methods known in the art such as with aqueous base, for example, aqueous sodium hydroxide. Similarly, where $R^2$ and/or $R^3$ represent a protecting group such as an acyl or aroyl group this can be removed by hydrolysis, for example with an alkali metal hydroxide such as potassium hydroxide, to yield the free hydroxyl compound.

As indicated above, the compounds of formula (II) are prepared in racemic or optically active form, depending on the form of the starting material of formula (III) and on whether chemical or microbial reduction is utilised. Where a recemate is obtained, it can be separated into its enantiomorphs in conventional manner, for example, by chemical resolution. The latter may be achieved by forming diastereoisomers from the racemic mixture, by reaction with an appropriate optically active resolving agent. Thus the free acids of formula (II) or (III) may be reacted with an optically active amine such as (−)-ephedrine or (+)- and (−)-α-methylbenzylamine, the difference in the solubility of the diastereoisomers obtained permitting selective re-crystallisation of one form and regeneration of the optically active acids of formula (II) or (III) from the mixture.

When it is desired to prepare a particular dihydroxy stereoisomer of formula (II), the appropriate enantiomer of formula (III) rather than the racemate will be normally chosen for reduction so as to reduce the resolution problems. Separation of the cis-type diol isomers of the compound of formula (II) from the trans-type diol isomer, and the resolved cis-diol and the resolved trans-diol, may be effected by chromotographic techniques, for example by column or by t.l.c. techniques using, for example, a silicic acid t.l.c. plate eluted with acetic acid; ethyl acetate; benzene (10:50:50 or 2:50:50). Visualisation can be accomplished by UV light (254 nm.) or by using a ceric sulphate/molybdic acid/sulphuric acid spray reagent and then heating the t.l.c. plate at 80° C.

The racemates and enantiomorphs of formula (II) and (III) and their salts and esters, possess useful pharmacological activity, especially spasmolytic activity, and this property coupled with their low toxicity, renders them useful in the treatment of such conditions as bronchial spasm and intestinal colic.

In addition, the compounds of formula (II) and (III) have been shown to possess anti-inflammatory and anti-allergic properties and accordingly are potentially useful in the therapy of rheumatoid conditions and immediate hypersensitivity diseases. Further, the compounds of formula (III), and their salts and esters, possess useful anti-thrombotic activity coupled with low toxicity which renders them useful in the treatment of thrombosis in animals especially humans. These activities have been demonstrated at doses from about 1 to 150mg./kg. depending on the test procedure used. In the treatment of humans, the effective dosage range will normally lie between 5 and 25 mg./kg. although other dosing schedules may be used at the discretion of the physician treating the patient.

In therapeutic use, the active compounds of the invention may be administered enterally, preferably orally, or parenterally, preferably intravenously, and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier or diluted by a carrier, or enclosed or encapsulated by a carrier, in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methylcullulose, polyoxyethylene sorbitan monolaurate, methyl- or propyl-hydroxybenzoate, ethyl cellulose acetate phthalate; low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 5 to 500 mg. (preferably 10–150 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

The following Examples illustrate the invention:

EXAMPLE 1

Triphenyl-2-oxoheptyl phosphonium bromide n-Butyl lithium in n-hexane, 15% w/w (416ml.) was added from a dropping funnel to a mechanically stirred suspension of triphenyl methyl phosphonium bromide (178.6 g.) in dry ether (1500 ml.) at 0°–5° C, under a nitrogen atmosphere.

With completion of additions, the solution was stirred for 15 minutes then n-hexanoyl chloride (34.5ml.) in dry ether (500ml.) was added dropwise at 0°–5° C, to the stirred solution, still under nitrogen. This was stirred for 30 minutes after which enough water (ca.250ml.) was added to allow two phases to form. The ether phase was washed with an aqueous solution of sodium chloride, dried with anhydrous sodium sulphate, and then evaporated to an oil. I.R.) max. 1540 cm$^{-1}$.

This oil dissolved in chloroform (300 ml.) was shaken with a 1.2 Molar solution of hydrogen bromide in water (500ml.), the chloroform phase was run off, washed with sodium chloride solution, dried with anhydrous sodium sulphate, and then evaporated to an oil. Two successive cold ether triturations, and three successive hot benzene triturations gave a white solid (38.4g.). After filtration and drying at 45° C under vacuum the melting point was found to be 193° C. Recrystallisation from carbon tetrachloride/chloroform to which 40/60° petroleum ether was added gave pure triphenyl-2-oxoheptyl phosphonium bromide (m.p. 195° C).

EXAMPLES 2 to 5

The following phosphoranes were prepared from phosphonium bromide salts obtained by processes similar to that described in Example 1. The phosphorane was liberated from the phosphonium bromide salt with 5M sodium hydroxide.

Acetyl methylene triphenyl phosphorane (m.p.206° C.) (Ex.2)

5-Methoxycarbonyl-n-pentanoyl methylene triphenylphosphorane (Ex.3)

n-Octanoylmethylene triphenyl phosphorane (Ex.4)

In addition, the phosphonium bromide salt obtained by the process of Example 1 was converted to the corresponding phosphorane n-Hexanoylmethylene triphenyl phosphorane (Ex.5)

Each of the above phosphoranes were characterised by spectroscopic methods, for instance, the C=O stretching frequency in their I.R. spectra at 1540 cm$^{-1}$. This was in full agreement with N.M.R. data for the compounds.

The products of Examples 3 to 5 were oils.

EXAMPLE 6

Preparation of 3-(3-hydroxy-5-oxo-2-(3-oxooct-2-enyl) cyclo pent-1-enyl) propanoic acid 3-(2-Formyl-3-hydroxy-5-oxo-cyclopent-1-enyl) propanoic acid (14.0g.) (prepared as described in our co-pending U.S. application Ser. No. 459829) was dissolved in redistilled dry T.H.F (100ml.) and treated with dropwise additions of n-hexanoylmethylene triphenyl phosphorane (prepared from triphenyl-2-oxoheptyl phosphonium bromide (32.0g.) by treatment with 5M NaOH) in redistilled dry T.H.F. (100ml.). The solution was stirred at 0° C. for 2 hours and then at 25° C. for 70 hours.

The mixture was rotary evaporated to an oil which was dissolved in excess NaHCO$_3$ solution and shaken with chloroform. The aqueous phase was acidified with citric acid solution to pH4 and shaken four times with ethyl acetate. The ethyl acetate phases were combined, washed with saturated NaCl solution, dried over anhydrous MgSO$_4$ and rotary evaporated to an oil. The oil was dissolved in chloroform and cooled. Crystallisation occurred to give a white solid (11.3g.) (52%) m.p. 57–8° C.; I.R. $\nu$ max. 2940, 1730, 1710, 1670 cm$^{-1}$, U.V. $\lambda$ max. (MeOH) 287nm ($\epsilon$27,400).

The compound was 3-[3-hydroxy-5-oxo-2-(3-oxooct-1-enyl) cyclopent-1-enyl]propanoic acid (m.p. 57° C.).

EXAMPLE 7

Dimethyl-(2-oxoheptyl) phosphonate (obtained from Aldrich Chemical Company, Inc.) was treated with dry dimethoxyethane washed sodium hydride in dry dimethoxy ethane. 3-(2-Formyl-3-hydroxy-5-oxo-cyclopent-1-enyl)propanoic acid in dry dimethoxy ethane was then added to the reaction mixture.

The mixture was stirred for 18 hours at room temperature and worked up as in Example 6; NaHCO$_3$ extraction, citric acid acidification and ethyl acetate extraction. The product was chromatographed on silicic acid to yield 3-[3-hydroxy-5-oxo-2-(3-oxooct-1-enyl)cyclopent-1-enyl] propanoic acid (m.p. 57° C.).

EXAMPLE 8 n-Butyl lithium (12.1 ml.) (8.8g./100ml.) was added dropwise over 10 minutes to a stirred, ice-cooled suspension of methyltriphenylphosphonium bromide (5.4g.) in dry ether (50ml.) under a nitrogen atmosphere. Stirring was continued for 20 minutes, then 5-hydroxyhexanoic acid lactone (1.5g.) in dry ether was added over 10 minutes. Once again stirring was continued for half-an-hour and then chloroform and water were added to form two clear layers. The organic phase was separated and washed once with water. Drying (MgSO$_4$) and evaporation gave an oil (6-hydroxy-2-oxoheptylidene triphenylphosphorane).

The infra-red spectrum of the above phosphorane exhibited a characteristic peak at 1,540 cm$^{-1}$.

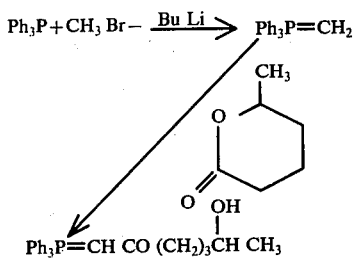

EXAMPLE 9

Methyl-3-[2-formyl-3-hydroxy-5-oxo-cyclopent-1-enyl] propanoate, prepared as in Example 6 of our copending application Ser. No. 459,829, was reacted with n-hexanoyl methylene triphenyl phosphorane as in Example 6, to yield methyl-3-[3-hydroxy-5-oxo-2-(3-oxaoct-1-enyl) cyclopent-1-enyl] propanoate as an oil. U.V. λmax. (MeOH) 287.nm (ε, 26,000); I.R.(film) ν max. 3450, 1740 and 1710 cm$^{-1}$.

The reaction was accomplished using the same reaction conditions as those adopted in Example 6 except that the acidification with citric acid was omitted and the ester product was purified by column chromatography on silicic acid.

EXAMPLE 10

The methyl ester starting material of Example 9 was reacted with 2,3-dihydropyran in the presence of p-toluene sulphonic acid as catalyst, using as solvent dry methylene chloride to yield the tetrahydropyranyl ether. This was then reacted with n-hexanoyl-methylene triphenyl phosphorane using the method of Example 9.

The final product of the reaction was methyl-[5-oxo-2-(3-oxooct-1-enyl)-3-(2-tetrahydropyranyloxy) cyclopent-1-enyl] propanoate (m.p. 60° C.).

EXAMPLE 11 and 12

The procedure of Example 6 was repeated except that instead of racemic 3-(2-formyl-3-hydroxy-5-oxo-cyclopent-1-enyl) propanoic acid there was used the (+)-and (−)- forms of the acid as starting material. The products of the two reactions were (+)-3-[3-hydroxy-5-oxo-2-(3-oxooct-1-enyl) cyclopent-1-enyl] propanoic acid m.p. 73° C.[α]$_D^{25}$ +37° and the corresponding (−) stereoisomer m.p. 73° C.[α]$_D^{25}$ −35°.

EXAMPLES 13 to 16

The aldehyde 3-(2-formyl-3-hydroxy-5-oxo-cyclopent-1-enyl) propanoic acid was reacted with the phosphoranes shown below:

| Example No. | Phosphorane |
| --- | --- |
| 13 | Ph$_3$P = CH . CO CH$_3$ |
| 14 | Ph$_3$P = CH . CO C$_7$H$_{15}$ |
| 15 | Ph$_3$P = CH . CO (CH$_2$)$_4$COOCH$_3$ |
| 16 | Ph$_3$P = CH . CO CH(C$_2$H$_5$) (CH$_2$)$_3$ CH$_3$ |

The reactions were carried out using the procedure of Example 6. The products of the reactions were as follows:

3-[3-Hydroxy-5-oxo-2-(3-oxobut-1-enyl)cyclopent-1-enyl] propanoic acid (m.p. 132–4° C.) (Example 13).

3-[3-Hydroxy-5-oxo-2-(3-oxodec-1-enyl) cyclopent-1-enyl] propanoic acid (m.p. 93° C.) (Example 14).

3-[3-Hydroxy-5-oxo-2-(7-methoxycarbonyl-3-oxohept-1-enyl) cyclopent-1-enyl] propanoic acid (m.p. 100°–102° C.) (Example 15).

3-[3-Hydroxy-5-oxo-2-(4-ethyl-3-oxooct-1-enyl)cyclopent-1-enyl] propanoic acid (U.V. λ max. 294nm.) (ε18,100) (Example 16).

EXAMPLE 17

The phosphorane (1.9g.) obtained in Example 8 and 3-(2-formyl-3-hydroxy-5-oxo-cyclopent-1-enyl) propanoic acid (0.54 g.) were dissolved in tetrahydrofuran and stirred at room temperature. After 1½ hours thin layer chromatography showed that only a small amount of aldehyde remained. The solvent was removed under vacuum to leave an oil which was 3-[3-hydroxy-5-oxo-2-(7-hydroxy-3-oxooct-1-enyl) cyclopent-1-enyl] propanoic acid. T.l.c. and UV (λ max. 289 nm.) supported the structural assignment of the product of this reaction.

EXAMPLE 18

3-[3-Hydroxy-5-oxo-2-(7-methoxycarbonyl-3-oxohept-1-enyl) cyclopent-1-enyl] propanoic acid (2.0 g.) in methanol (100 ml.) was reacted with p-toluene sulphonic acid at room temperature for 18 hours. Removal of the solvent gave an oil which was purified on a silicic acid column using chloroform as an eluent. The isolated product was methyl-3-[hydroxy-5-oxo-2-(7-methoxycarbonyl-3-oxo-hept-1-enyl) cyclopent-1-enyl] propanoate Calculated % C: 61.34, H: 6.86, O: 31.80; Found % C: 61.10, H: 7.06, O: 31.77.

EXAMPLE 19

3-[3-Hydroxy-5-oxo-2-(7-methoxycarbonyl-3-oxo-hept-1-enyl) cyclopent-1-enyl] propanoic acid (2.0 g.) in water (40ml.) was treated with 0.1 M NaOH (144ml.) at 0° C. This mixture was stirred for 65 minutes at 0° C. and then acidified to pH2 with 1M HCl. The mixture was then extracted with ethyl acetate and the organic phase washed with magnesium sulphate and rotary evaporated to an oil. On cooling, crystals of 3-[3-hydroxy-5-oxo-2-(7-carboxy-3-oxohept-1-enyl) cyclopent-1-enyl] propanoic acid (m.p. 110° C.) were deposited.

EXAMPLE 20

Methyl-3-[3-hydroxy-5-oxo-2-(7-methoxycarbonyl-3-oxohept-1-enyl) cyclopent-1-enyl] propanoate obtained by the process of Example 18, was dissolved in dry redistilled tetrahydrofuran. Chlorodimethyl-silane and 1,1,1-3,3,3-hexamethyldisilazane were added to the solution and the reaction mixture stirred at room temperature overnight. The silyl ether of the ester starting material was shown to have been produced (by G.C.-M.S).

EXAMPLE 21

Methyl-3-[3-p-chlorobenzoyloxy)-5-oxo-2-(β-styryl)-cyclopent-1-enyl] propanoate was prepared by the process of Example 6 of our co-pending application Ser. No. 459,829. This compound (1g.) in water: dioxan (10ml:40ml) was treated with 1% osmium tetroxide solution (1.9ml). After one hour portions of sodium periodate were added. The reaction mixture was left for 2 days and thereafter filtered to remove inorganic material and separated from benzaldehyde by column chromatography. The product of the reaction was methyl-3-[3-p-chlorobenzoyloxy)-5-oxo-2-formyl-cyclopent-1-enyl] propanoate.

EXAMPLE 21(a)

The product of Example 21 was treated with acetyl methylene triphenyl phosphorane (prepared as in Example 2) in chloroform/tetrahydrofuran (equal volumes). The reaction mixture was stirred at room temperature for 18 hours. The mixture was rotary evaporated to an oil which was then chromatographed on silicic acid using a 1:1 toluene/chloroform eluent. Appropriate fractions were combined to give the product (Methyl-3-[3-(p-chlorobenzoyloxy)-5-oxo-2-(3-oxo-but-1-enyl)-cyclopent-1-enyl] propanoate.

Spectroscopic data, for example infra red spectra, NMR, Ultra violet, was in accordance with the above structure of the product of the Wittig reaction.

EXAMPLE 22

3-[3-Hydroxy-5-oxo-2-(3-oxo oct-1-enyl)cyclopent-1-enyl] propanoic acid (1.0g.) in water (26ml.) and ethanol (3ml.) containing triethylamine (340mg.) was stirred at 0° C. and treated with sodium borohydride (130mg.) dissolved in cold water (3ml.). The reducing agent was added in small portions over a period of 10 minutes and then the reaction mixture was stirred for 1 hour at a temperature below room temperature.

The solution was poured into cold excess citric acid solution containing ethyl acetate. After stirring for 30 minutes, the ethyl acetate was separated and washed with saturated brine, dried over anhydrous magnesium sulphate and rotary evaporated to an oil.

The oil was purified by chromatography on a silicic acid column using 2% methanol in chloroform. The appropriate fractions were then combined and rotary evaporated to an oil. The product was 3-[3-hydroxy-5-oxo-2-(3-hydroxy-oct-1-enyl)cyclopent-1-enyl] propanoic acid.

Calculated % C:64.85, H:8.16, O:27.00; Found % C:64.60, H:8.41, O:26.99.

EXAMPLE 23

Chromatographic separation of the cis/trans isomers of 3-[3-Hydroxy-5-oxo-2-(3-hydroxy-oct-1-enyl) cyclopent-1-enyl] propanoic acid The purified oil was placed on a column of silicic acid made up in 20% ethyl acetate in toluene. The concentration of ethyl acetate in toluene was slowly increased during elution of the column. In the range of 30 to 40% ethyl acetate, separation of the diastereoisomers was achieved.

Optionally a fraction collector was used to collect the fractions with 35% ethylacetate/toluene.

Employing the above chromatography step, separation of the cis and trans isomers was achieved.

EXAMPLE 24

The process of Example 6 was repeated with the resolved aldehyde starting materials. The 3-oxo material thus formed was then reduced by the process of Example 22. The reduced reaction products were then separated as in Example 23 into the four stereoisomers depicted below:

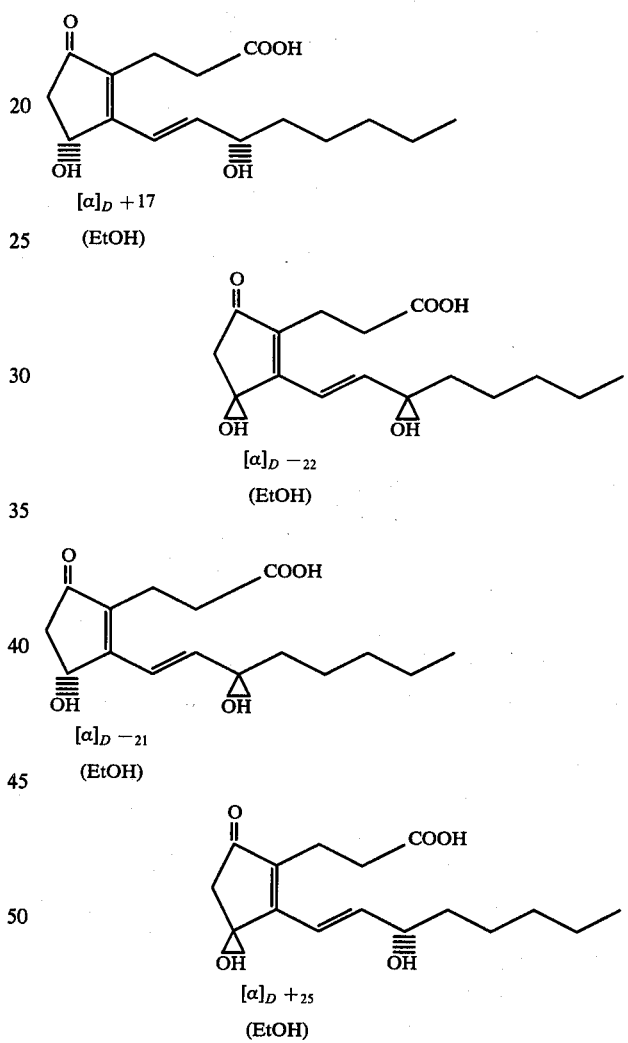

$[\alpha]_D$ +17
(EtOH)

$[\alpha]_D$ −22
(EtOH)

$[\alpha]_D$ −21
(EtOH)

$[\alpha]_D$ +25
(EtOH)

All compounds were oils and possessed identical IR and UV spectra, for example UV (MeOH). λ max.276nm (ε values ranged from 17,000 to 18,000).

EXAMPLE 25

Microbial reduction of 3-[3-Hydroxy-5-oxo-2-(3-oxaoct-1-enyl) cyclopent-1-enyl] propanoic acid 3-[3-Hydroxy-5-oxo-2-(3-oxaoct-1-enyl)cyclopent-1-enyl] propanoic acid (0.50g.) in aqueous acetone was added to a culture of *Pseudomonas sp.* NRRL B-3875 in the growth medium set out below:

| | |
|---|---|
| Glucose (10g.) in 250 ml. water | |
| Ammonium Sulphate (5g.) | |
| Magnesium Sulphate (0.5g.) | in 250 ml. |
| Dipotassium Hydrogen Phosphate (3.5g.) | water |
| Monopotassium Dyhydrogen Phosphate (1.5g.) | |

The solution of glucose in water and the solution of sulphates and phosphates were sterilised separately and then combined. The mixture was allowed to ferment in 25ml. conical flasks (each containing 15ml. of solution -15mg. of starting material in 15ml. of culture solution) for 12 days at 25° C. after which time the mixture was centrifuged and decanted. The solution was acidified with citric acid to pH3 and extracted five times with ethyl acetate. The combined organic phases were washed with a little saturated sodium chloride solution, dried over anhydrous magnesium sulphate and rotary evaporated to an oil.

The oil was dissolved in 2% methanol in chloroform and chromatographed on a silicic acid column. The first main fractions contained optically active 3-[3-hydroxy-5-oxo-2-(3-oxaoct-1-enyl)cyclopent-1-enyl] propanoic acid (163mg.).

Further fractions contained optically active 3-[3-hydroxy-5-oxo-2-(3-hydroxy-oct-1-enyl)cyclopent-1-enyl] propanoic acid (68mg.) $[\alpha]_D^{22}$ +24.2 (EtOH) U.V. (MeOH) $\lambda$ max.277 nm. ($\epsilon$16,600).

EXAMPLES 26 to 33

Using the reductive method of Example 22, together with appropriate alkylation or acylation, where necessary, the following further compounds were prepared.

Ethyl-3-[3-hydroxy-5-oxo-2-(3-hydroxy-oct-1-enyl) cyclopent-1-enyl] propanoate. U.V.$\lambda$max. 275 nm. ($\epsilon$25,000)

Methyl-3-[3-acetoxy-5-oxo-2-(3-acetoxy-oct-1-enyl) cyclopent-1-enyl] propanoate. U.V.$\lambda$max. 272nm. ($\epsilon$21,900)

Methyl-3-[3-acetoxy-5-oxo-2-(3-acetoxy-7-methoxycarbonylhept-1-enyl)cyclopent-1-enyl] propanoate U.V.$\lambda$max. 270nm. ($\epsilon$25,800)

3-[3-Hydroxy-5-oxo-2-(3-hydroxy-7-methoxycarbonylhept-1-enyl) cyclopent-1-enyl] propanoic acid. U.V. $\lambda$ max. 275nm. ($\epsilon$19,700) Methyl 3-[3-hydroxy-5-oxo-2-(3-hydroxy-7-methoxycarbonyl hept-1-enyl)cyclopent-1-enyl]propanoate, U.V. $\lambda$ max. 275 nm.

Methyl 3-[3-hydroxy-5-oxo-2-(3-hydroxy-oct-1-enyl)-cyclopent-1-enyl]propanoate, U.V. $\lambda$max. 275 nm.

3-[3-Hydroxy-5-oxo-2-(7-carboxy-3-hydroxyhept-1-enyl)cyclopent-1-enyl]propanoic acid, U.V. $\lambda$max. 275 nm. 34

Ethyl 3-[3-hydroxy-5-oxo-2-(7-ethoxycarbonyl-3-hydroxyhept-1-enyl)cyclopent-1-enyl]propanoate, $\lambda$ max. 275 nm.

EXAMPLE 34

3-[3-Hydroxy-5-oxo-2-(3-oxobut-1enyl)cyclopent-1-enyl]propanoic acid (2.2g.-0.0092 mole) prepared as in Example 13 was dissolved in EtOH/H$_2$O (8:2) and the mixture cooled. Triethylamine (1.41ml.) was added. This was followed by the portionwise addition of sodium borofhydride (0.35g.-0.0092 mole) over 15 minutes with continuous stirring. Dilute oxalic acid was then added to bring the pH of the reaction solution to 3, the solution then being extracted three times with ethyl acetate, after saturating the aqueous phase with sodium chloride. The combined extracts were then washed three times with saturated sodium chloride solution, dried and evaporated to dryness.

Thin layer chromatography and NMR carried out on the purified product indicated that the product of the reaction was 3-[3-hydroxy-5-oxo-2-(3-hydroxy-but-1-enyl) cyclopent-1-enyl]propanoic acid.

EXAMPLE 35

Methyl 3-[3-hydroxy-5-oxo-2-(3-oxodec-1-enyl)cyclopent-1-enyl]propanoate (2.1g.) was dissolved in EtOH/H$_2$O 9:1 (30ml.) and chilled in an ice bath. Triethylamine (0.95ml.) was added followed by sodium borohydride (0.24g.) dissolved in water (2ml.). The reaction mixture was stirred for fifteen minutes and then water was added, followed by dilute oxalic acid solution to adjust the pH to 5. Ethyl acetate extraction, washing and drying of the extract followed by evaporation gave an oil. This was chromatographed on silicic acid, using as an eluent: MeOH/CHCl$_3$. The appropriate fractions containing the major component were combined and evaporated to dryness ($\sim$800mg.oil). This was rechromatographed using a similar column. In this way, pure Methyl 3-[3-hydroxy-5-oxo-2-(3-hydroxydec-1-enyl) cyclopent-1-enyl]propanoate was obtained. Spectroscopic data was in full accord with the expected structure of the final product.

EXAMPLE 36

3-[3-Hydroxy-5-oxo-2-(3-oxodec-1-enyl)cyclopent-1-enyl]propanoic acid (2.0g.-0.0062 mole) was dissolved in EtOH/H$_2$O 9:1 (30ml.). Triethylamine (0.9ml,0.0068 mole) was added followed by the portionwise addition of sodium borohydride (0.24g. 0.0062 mole) over 10 minutes. After 30 minutes thin layer chromatography indicated that very little starting material remained. 30ml. of water was then added to the reaction mixture and the solution acidified to pH3 by addition of dilute oxalic acid solution. The solution was saturated in sodium chloride solution and extracted twice with ethyl acetate. The combined extracts were then washed three times with a small quantity of saturated sodium chloride solution. Evaporation, after drying, of the ethyl acetate solution, gave an oil which was chromatographed on silicic acid, using 2% methanol in chloroform as eluent. The appropriate fractions were evaporated to dryness to give an oil which ultra violet, NMR and infra red spectroscopy confirmed as 3-[3-hydroxy-5-oxo-2-(3-hydroxydec-1-enyl)propanoic acid. U.V. $\lambda$max. 275 nm. ($\epsilon$25,000).

What is claimed is:

1. A compound of formula (II):

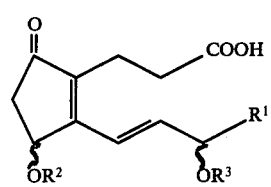

(II)

wherein R$^1$ is a C$_{1-8}$alkyl group optionally substituted by hydroxyl or COOH,and wherein R$^2$ and R$^3$ are individually hydrogen or a protecting group selected from the group consisting of acetyl, trimethylsilyl, p-chlorobenzoyl and tetrahydropyranyl; or a C$_{1-4}$alkyl ester thereof.

2. A compound of formula (II) according to claim 1 wherein R¹ is n-pentyl.

3. A compound of formula (II) according to claim 1 wherein R³ is hydrogen.

4. A compound of formula (II) according to claim 1 which is 3-[3-hydroxy-5-oxo-2-(3-hydroxy-oct-1-enyl)-cyclopent-1-enyl]propanoic acid.

5. A compound of formula (II) according to claim 1 which is 3-[3-hydroxy-5-oxo-2-(3-hydroxy-7-methoxycarbonyl hept-1-enyl)cyclopent-1-enyl]propanoic acid.

6. A compound of formula (III):

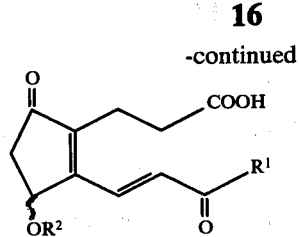

(III)

wherein
R¹ is a $C_{1-8}$ alkyl groups, optionally substituted by hydroxyl or COOH, and
wherein
R² is hydrogen or a protecting group selected from the group consisting of acetyl, trimethylsilyl, p-chlorobenzoyl and tetrahydropyranyl; or a $S_{1-3}$ alky ester thereof.

7. A compound of formula (III) according to claim 6 which is 3-[3-hydroxy-5-oxo-(3-oxooct-1-enyl)-cyclopent-enyl]propanoic acid.

* * * * *

UNITED STATES PATENT AND TRADEMARK OFFICE
CERTIFICATE OF CORRECTION

PATENT NO. : 4,039,571
DATED : August 2, 1977
INVENTOR(S) : William Dawson, et al.

It is certified that error appears in the above-identified patent and that said Letters Patent are hereby corrected as shown below:

Column 7, line 14, "methylcullulose" should read --methylcellulose--.

Column 9, line 38, "($\epsilon$, 26,000) should read --($\epsilon$, 26,600)--.

Column 13, line 52, "275 nm. 34" should read --276-- (delete "34").

Column 13, line 63, "borofhydride" should read --borohydride--.

Column 16, line 16, "$S_{1-3}$ alky" should read --$C_{1-3}$ alkyl--.

Signed and Sealed this

Eighteenth Day of December 1979

[SEAL]

Attest:

SIDNEY A. DIAMOND

Attesting Officer      Commissioner of Patents and Trademarks